(12) United States Patent
Cao et al.

(10) Patent No.: US 10,555,685 B2
(45) Date of Patent: Feb. 11, 2020

(54) METHOD AND APPARATUS FOR DETERMINING TISSUE MORPHOLOGY BASED ON PHASE ANGLE

(75) Inventors: Hong Cao, Savage, MN (US); Saurav Paul, Minneapolis, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

(21) Appl. No.: 13/584,368

(22) Filed: Aug. 13, 2012

(65) Prior Publication Data

US 2013/0023784 A1     Jan. 24, 2013

Related U.S. Application Data

(62) Division of application No. 11/966,320, filed on Dec. 28, 2007, now Pat. No. 8,290,578.

(51) Int. Cl.
*A61B 5/00*     (2006.01)
*A61B 5/053*    (2006.01)

(52) U.S. Cl.
CPC .................................. *A61B 5/053* (2013.01)

(58) Field of Classification Search
CPC ..... A61B 5/053; A61B 5/0536; A61B 5/0537; A61B 5/0538
USPC ............. 600/547; 606/34, 39, 41, 45, 46, 49
See application file for complete search history.

(56) References Cited

U.S. PATENT DOCUMENTS

| 2,184,511 A | 12/1939 | Bagno et al. |
| 3,316,896 A | 5/1967 | Thomasset |
| 3,949,736 A | 4/1976 | Vrana et al. |
| 4,641,649 A | 2/1987 | Walinsky et al. |
| 5,230,349 A | 7/1993 | Langberg |

(Continued)

FOREIGN PATENT DOCUMENTS

| EP | 1472976 | 11/2004 |
| EP | 1586281 | 4/2009 |

(Continued)

OTHER PUBLICATIONS

Avetall, Boaz et al., "The Effects of Electrode-Tissue Contact on Radiofrequency Lesion Generation", *PACE, vol. 20* Dec. 1997, 2899-2910

(Continued)

*Primary Examiner* — Max F Hindenburg
(74) *Attorney, Agent, or Firm* — Dykema Gossett PLLC

(57) ABSTRACT

A compensation circuit has a predetermined, known complex impedance and is located in a handle of a catheter or in a distal end of a cable that connects to the catheter. The compensation circuit is probed with a pilot signal produced by a compensation control. The compensation control measures the complex impedance, which is the combination of the circuit's known impedance as well as that of the cable and then determines the difference between the measured and the known complex impedances which represents that which is attributable to the cable, and is used to cancel out such cable-related contributions to complex impedance in other electrical connections in the same cable. In another aspect, an unknown tissue is identified as one of a plurality of possible tissue types such as regular myocardium, scar and fat based on the measured phase angle of the complex impedance of the unknown tissue.

14 Claims, 5 Drawing Sheets

(56) References Cited

U.S. PATENT DOCUMENTS

| | | | |
|---|---|---|---|
| 5,257,635 A | 11/1993 | Langberg | |
| 5,297,549 A | 3/1994 | Beatty et al. | |
| 5,311,866 A | 5/1994 | Kagan et al. | |
| 5,341,807 A | 8/1994 | Nardella | |
| 5,366,896 A | 11/1994 | Margrey | |
| 5,423,808 A | 6/1995 | Edwards et al. | |
| 5,429,131 A | 7/1995 | Scheinman et al. | |
| 5,447,529 A | 9/1995 | Marchlinski et al. | |
| 5,462,544 A | 10/1995 | Saksena et al. | |
| 5,546,940 A | 8/1996 | Panescu et al. | |
| 5,562,721 A | 10/1996 | Marchlinski et al. | |
| 5,582,609 A | 12/1996 | Swanson et al. | |
| 5,588,432 A | 12/1996 | Crowley | |
| 5,630,034 A | 5/1997 | Oikawa et al. | |
| 5,657,755 A | 8/1997 | Desai | |
| 5,659,624 A | 8/1997 | Fazzari et al. | |
| 5,673,704 A | 10/1997 | Marchlinski et al. | |
| 5,688,267 A | 11/1997 | Panescu et al. | |
| 5,697,377 A | 12/1997 | Wittkampf | |
| 5,702,386 A | 12/1997 | Stern et al. | |
| 5,718,241 A | 2/1998 | Ben-Haim et al. | |
| 5,722,402 A | 3/1998 | Swanson et al. | |
| 5,730,127 A | 3/1998 | Avitall | |
| 5,759,159 A | 6/1998 | Masreliez | |
| 5,782,900 A | 7/1998 | de la Rama et al. | |
| 5,800,350 A * | 9/1998 | Coppleson et al. | 600/372 |
| 5,810,742 A * | 9/1998 | Pearlman | 600/547 |
| 5,814,043 A | 9/1998 | Shapeton | |
| 5,836,943 A | 11/1998 | Miller, III | |
| 5,836,990 A | 11/1998 | Li | |
| 5,837,001 A | 11/1998 | Mackey | |
| 5,846,238 A | 12/1998 | Jackson et al. | |
| 5,904,709 A | 5/1999 | Arndt et al. | |
| 5,944,022 A | 8/1999 | Nardella et al. | |
| 5,954,665 A | 9/1999 | Ben-Haim | |
| 6,001,093 A | 12/1999 | Swanson et al. | |
| 6,019,757 A | 2/2000 | Scheldrup | |
| 6,026,323 A * | 2/2000 | Skladnev et al. | 600/547 |
| 6,035,341 A | 3/2000 | Nunally et al. | |
| 6,063,078 A | 5/2000 | Wittkampf | |
| 6,129,669 A | 10/2000 | Panescu et al. | |
| 6,171,304 B1 | 1/2001 | Netherly et al. | |
| 6,179,824 B1 | 1/2001 | Eggers et al. | |
| 6,206,874 B1 | 3/2001 | Ubby et al. | |
| 6,217,574 B1 | 4/2001 | Webster | |
| 6,217,576 B1 | 4/2001 | Tu et al. | |
| 6,221,070 B1 | 4/2001 | Tu et al. | |
| 6,226,542 B1 | 5/2001 | Reisfeld | |
| 6,233,476 B1 | 5/2001 | Strommer et al. | |
| 6,246,896 B1 | 6/2001 | Dumoulin et al. | |
| 6,256,540 B1 | 7/2001 | Panescu et al. | |
| 6,322,558 B1 | 11/2001 | Taylor et al. | |
| 6,337,994 B1 | 1/2002 | Stoianovici et al. | |
| 6,391,024 B1 | 5/2002 | Sun et al. | |
| 6,423,057 B1 | 7/2002 | He et al. | |
| 6,427,089 B1 | 7/2002 | Knowlton | |
| 6,443,894 B1 | 9/2002 | Sumanaweera et al. | |
| 6,445,952 B1 | 9/2002 | Manrodt et al. | |
| 6,456,864 B1 | 9/2002 | Swanson et al. | |
| 6,468,271 B1 | 10/2002 | Wentzel et al. | |
| 6,471,693 B1 | 10/2002 | Carroll et al. | |
| 6,475,215 B1 | 11/2002 | Tanrisever | |
| 6,490,474 B1 | 12/2002 | Willis et al. | |
| 6,498,944 B1 | 12/2002 | Ben-Haim et al. | |
| 6,507,751 B2 | 1/2003 | Blume et al. | |
| 6,511,478 B1 | 1/2003 | Burnside et al. | |
| 6,546,270 B1 | 4/2003 | Goldin et al. | |
| 6,558,382 B2 | 5/2003 | Jahns et al. | |
| 6,569,160 B1 | 5/2003 | Goldin et al. | |
| 6,575,969 B1 | 6/2003 | Rittman, III et al. | |
| 6,605,082 B2 | 8/2003 | Hareyama et al. | |
| 6,652,518 B2 | 11/2003 | Wellman et al. | |
| 6,663,622 B1 | 12/2003 | Foley et al. | |
| 6,676,654 B1 | 1/2004 | Balle-Petersen et al. | |
| 6,683,280 B1 | 1/2004 | Wofford | |
| 6,690,963 B2 | 2/2004 | Ben-Haim et al. | |
| 6,696,844 B2 | 2/2004 | Wong et al. | |
| 6,712,074 B2 | 3/2004 | Edwards et al. | |
| 6,743,225 B2 | 6/2004 | Sanchez et al. | |
| 6,755,790 B2 | 6/2004 | Stewart et al. | |
| 6,780,182 B2 | 8/2004 | Bowman et al. | |
| 6,788,967 B2 | 9/2004 | Ben-Haim et al. | |
| 6,813,515 B2 * | 11/2004 | Hashimshony | 600/547 |
| 6,840,938 B1 | 1/2005 | Morley et al. | |
| 6,917,834 B2 | 7/2005 | Koblish et al. | |
| 6,918,876 B1 | 7/2005 | Kamiyama | |
| 6,926,669 B1 * | 8/2005 | Stewart et al. | 600/439 |
| 6,936,047 B2 | 8/2005 | Nasab et al. | |
| 6,950,689 B1 | 9/2005 | Willis et al. | |
| 6,964,867 B2 | 11/2005 | Downs | |
| 6,965,795 B2 | 11/2005 | Rock | |
| 6,993,384 B2 | 1/2006 | Bradley et al. | |
| 7,041,096 B2 | 5/2006 | Malis et al. | |
| 7,106,043 B1 * | 9/2006 | Da Silva et al. | 324/72.5 |
| 7,197,354 B2 | 3/2007 | Sobe | |
| 7,248,032 B1 * | 7/2007 | Hular et al. | 324/72.5 |
| 7,263,395 B2 | 8/2007 | Chan et al. | |
| 7,263,397 B2 | 8/2007 | Hauck et al. | |
| 7,386,339 B2 | 6/2008 | Strommer et al. | |
| 7,497,858 B2 | 3/2009 | Chapelon et al. | |
| 7,499,745 B2 * | 3/2009 | Littrup et al. | 600/547 |
| 7,536,218 B2 | 5/2009 | Govari et al. | |
| 7,565,613 B2 | 7/2009 | Forney | |
| 7,610,078 B2 | 10/2009 | Willis | |
| 7,633,502 B2 | 12/2009 | Willis et al. | |
| 7,671,871 B2 | 3/2010 | Gonsalves | |
| 7,776,034 B2 | 8/2010 | Kampa | |
| 7,819,870 B2 | 10/2010 | Thao et al. | |
| 7,865,236 B2 * | 1/2011 | Cory et al. | 600/547 |
| 7,904,174 B2 | 3/2011 | Hammill et al. | |
| 7,925,349 B1 * | 4/2011 | Wong | A61B 5/02028 600/547 |
| 7,953,495 B2 | 5/2011 | Sommer et al. | |
| 8,403,925 B2 | 3/2013 | Miller | |
| 2001/0034501 A1 | 10/2001 | Tom | |
| 2001/0039413 A1 | 11/2001 | Bowe | |
| 2001/0047129 A1 | 11/2001 | Hall et al. | |
| 2001/0051774 A1 | 12/2001 | Littrup et al. | |
| 2002/0013537 A1 * | 1/2002 | Rock | A61B 5/05 600/547 |
| 2002/0022836 A1 | 2/2002 | Goble et al. | |
| 2002/0049375 A1 | 4/2002 | Strommere et al. | |
| 2002/0068931 A1 | 6/2002 | Wong et al. | |
| 2002/0072686 A1 | 6/2002 | Hoey et al. | |
| 2002/0077627 A1 | 6/2002 | Johnson et al. | |
| 2002/0120188 A1 | 8/2002 | Brock et al. | |
| 2002/0123749 A1 | 9/2002 | Jain | |
| 2002/0151887 A1 | 10/2002 | Stern et al. | |
| 2002/0177847 A1 | 11/2002 | Long | |
| 2003/0028183 A1 | 2/2003 | Sanchez et al. | |
| 2003/0045871 A1 | 3/2003 | Jain et al. | |
| 2003/0060696 A1 | 3/2003 | Skladnev et al. | |
| 2003/0065364 A1 | 4/2003 | Wellman et al. | |
| 2003/0093067 A1 | 5/2003 | Panescu et al. | |
| 2003/0093069 A1 | 5/2003 | Panescu et al. | |
| 2003/0100823 A1 | 5/2003 | Kipke et al. | |
| 2003/0109871 A1 | 6/2003 | Johnson et al. | |
| 2003/0130711 A1 | 7/2003 | Pearson et al. | |
| 2003/0187430 A1 | 10/2003 | Vorisek | |
| 2004/0006337 A1 | 1/2004 | Nasab et al. | |
| 2004/0030258 A1 | 2/2004 | Williams et al. | |
| 2004/0044292 A1 | 3/2004 | Yasushi et al. | |
| 2004/0078036 A1 | 4/2004 | Keidar | |
| 2004/0078058 A1 | 4/2004 | Holmstrom et al. | |
| 2004/0082946 A1 | 4/2004 | Malis et al. | |
| 2004/0087975 A1 | 5/2004 | Lucatero et al. | |
| 2004/0097806 A1 | 5/2004 | Hunter et al. | |
| 2004/0147920 A1 | 7/2004 | Keidar | |
| 2004/0181165 A1 | 9/2004 | Hoey et al. | |
| 2004/0243018 A1 | 12/2004 | Organ et al. | |
| 2004/0243181 A1 | 12/2004 | Conrad et al. | |
| 2004/0267252 A1 | 12/2004 | Washington et al. | |
| 2005/0010263 A1 | 1/2005 | Schauerte | |
| 2005/0054944 A1 | 3/2005 | Nakada et al. | |

(56) References Cited

U.S. PATENT DOCUMENTS

| | | | |
|---|---|---|---|
| 2005/0065507 A1 | 3/2005 | Hartley et al. | |
| 2005/0222554 A1 | 10/2005 | Wallace et al. | |
| 2006/0011669 A1 | 1/2006 | Massey | |
| 2006/0015033 A1 | 1/2006 | Blakley et al. | |
| 2006/0085049 A1 | 4/2006 | Cory et al. | |
| 2006/0173251 A1 | 8/2006 | Govari et al. | |
| 2006/0200049 A1 | 9/2006 | Leo et al. | |
| 2006/0235286 A1* | 10/2006 | Stone et al. | 600/381 |
| 2007/0016006 A1 | 1/2007 | Shachar | |
| 2007/0055142 A1 | 3/2007 | Webler | |
| 2007/0073179 A1 | 3/2007 | Afonso et al. | |
| 2007/0083193 A1 | 4/2007 | Werneth et al. | |
| 2007/0100332 A1 | 5/2007 | Paul et al. | |
| 2007/0106289 A1 | 5/2007 | O'Sullivan | |
| 2007/0118100 A1 | 5/2007 | Mahesh et al. | |
| 2007/0123764 A1 | 5/2007 | Thao et al. | |
| 2007/0161915 A1 | 7/2007 | Desai | |
| 2007/0225558 A1 | 9/2007 | Hauck et al. | |
| 2007/0225593 A1 | 9/2007 | Porath et al. | |
| 2007/0244479 A1 | 10/2007 | Beatty et al. | |
| 2007/0255162 A1 | 11/2007 | Abboud et al. | |
| 2008/0091193 A1 | 4/2008 | Kauphusman et al. | |
| 2008/0097220 A1 | 4/2008 | Lieber et al. | |
| 2008/0097422 A1 | 4/2008 | Edwards et al. | |
| 2008/0132890 A1 | 6/2008 | Woloszko et al. | |
| 2008/0183071 A1 | 7/2008 | Strommer et al. | |
| 2008/0183189 A1 | 7/2008 | Teichman et al. | |
| 2008/0221440 A1 | 9/2008 | Iddan et al. | |
| 2008/0234564 A1 | 9/2008 | Beatty et al. | |
| 2008/0234574 A1* | 9/2008 | Hancock | A61B 5/0507 600/430 |
| 2008/0249536 A1 | 10/2008 | Stahler et al. | |
| 2008/0275465 A1 | 11/2008 | Paul et al. | |
| 2008/0288023 A1 | 11/2008 | John | |
| 2008/0288038 A1 | 11/2008 | Paul et al. | |
| 2008/0300589 A1 | 12/2008 | Paul et al. | |
| 2008/0312713 A1 | 12/2008 | Wilfley et al. | |
| 2009/0012533 A1 | 1/2009 | Barbagli et al. | |
| 2009/0036794 A1 | 2/2009 | Stubhaug et al. | |
| 2009/0163904 A1 | 6/2009 | Miller et al. | |
| 2009/0171235 A1 | 7/2009 | Schneider et al. | |
| 2009/0171345 A1 | 7/2009 | Miller et al. | |
| 2009/0177111 A1 | 7/2009 | Miller et al. | |
| 2009/0247942 A1 | 10/2009 | Kirschenman | |
| 2009/0247943 A1 | 10/2009 | Kirschenman et al. | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman | |
| 2009/0275827 A1 | 11/2009 | Aiken et al. | |
| 2009/0276002 A1 | 11/2009 | Sommer et al. | |
| 2009/0306655 A1 | 12/2009 | Stangenes et al. | |
| 2010/0069921 A1 | 3/2010 | Miller et al. | |
| 2010/0168550 A1 | 7/2010 | Byrd et al. | |
| 2010/0168735 A1 | 7/2010 | Deno et al. | |
| 2010/0191089 A1 | 7/2010 | Stebler et al. | |
| 2010/0256558 A1 | 10/2010 | Olson et al. | |
| 2010/0274239 A1 | 10/2010 | Paul et al. | |
| 2010/0298823 A1 | 11/2010 | Cao et al. | |
| 2011/0015569 A1 | 1/2011 | Kirschenman et al. | |
| 2011/0118727 A1 | 5/2011 | Fish et al. | |
| 2011/0313311 A1 | 12/2011 | Gaw | |
| 2011/0313417 A1 | 12/2011 | de la Rama et al. | |
| 2012/0158011 A1 | 6/2012 | Sandhu et al. | |

FOREIGN PATENT DOCUMENTS

| | | |
|---|---|---|
| JP | 3585491 | 11/2004 |
| JP | 2005-279256 | 10/2005 |
| WO | 1998/046149 | 10/1998 |
| WO | 2000/078239 | 12/2000 |
| WO | 2007/067628 | 6/2007 |
| WO | WO-2007/067941 | 6/2007 |
| WO | WO-2009/065140 | 5/2009 |
| WO | 2009085457 A1 | 7/2009 |
| WO | WO-2009/085457 | 7/2009 |
| WO | 2009/120982 | 10/2009 |
| WO | 2011/123669 | 10/2011 |

OTHER PUBLICATIONS

Chakraborty, D. P., "ROC curves predicted by a model of visual search", *Institute of Pysics Publishing, Phys. Med. Biol.* 51 2006, 3463-3482.

Cho, Sungbo et al., "Design of electrode array for impedance measurement of lesions in arteries", *Physiol. Mease.* 26 S19-S26 doi: 10.088/0967-3334/26/2/002 2005.

Dumas, John H. et al., "Myocardial electrical impedance as a predictor of the quality of RF-induced linear lesions", *Physiological Measurement*, vol. 29 2008, Abstract only.

Fenici, R. R. et al., "Biomagnetically localizable multipurpose catheter and method for MCG guided intracardiac electrophysiology, biopsy and ablation of cardiac arrhythmias", *International Journal of Cardiac Imaging* 7 1991, 207-215.

Gales, Rosemary et al., "Use of bioelectrical impedance analysis to assess body composition of seals", *Marine Mammal Science*, vol. 10, Issue 1, Abstract Aug. 26, 2006.

Gao, Xin et al., "Computer-Assisted Quantative Evaluation of Therapeutic Responses for Lymphoma Using Serial PET/CT Imaging", *NIH Public Access, Acad Radiol.* 17(4) Apr. 2010, 1-21.

He, Ding S. et al., "Assessment of Myocardial Lesion Size during In Vitro Radio Frequency Catheter Ablation", *IEEE Transactions on Biomedical Engineering*, vol. 50, No. 6 Jun. 2003, 768-776.

Himel, Herman D., "Development of a metric to assess completeness of lesions produced by radiofrequency albation in the heart", *Dept. of Biomedical Engineering, University of NC, Chapel Hill* 2006, i-xvii; 1-138.

Holmes, Douglas et al., "Tissue Sensing Technology Enhances Lesion Formation During Irrigated Catheter Albation", *HRS* 2008, Abstract only.

Masse, Stephane et al., "A Three-dimensional display for cardiac activation mapping", *Pace*, vol. 14 Apr. 1991.

Salazar, Y et al., "Transmural versus nontransmural in situ electrical impedance spectrum for healthy, ischemic, and healed myocardium", *IEEE Xplore, Abstract* 2009.

Zheng, Xiangsheng et al., "Electrode Impedance: An Indicator of Electrode-Tissue Contact and Lesion Dimensions During Linear Ablation", *Journal of Electrophysiology* 4 2000, 645-654.

PCT/US2006/061714 International Search Report and Written Opinion dated Sep. 22, 2008.

PCT/US2008/084194 International Search Report dated Feb. 5, 2009.

PCT/US2011/047235 International Search Report and Written Opinion dated Dec. 14, 2011.

Supplemental European Search Report for EP Application No. 11842330.0, dated Jan. 20, 2014. 9 pages.

Thomas, Stuart P., et al., Comparison of Epicardial and Endocardial Linear Ablation Using Handheld Probes, The Annals of Thoracic Surgery, vol. 75, Issue 2. pp. 543-548, Feb. 2003.

International Search Report for PCT Application No. PCT/US2006/046565, dated May 2, 2007. 1 page.

International Search Report and Written Opinion for PCT Application No. PCT/US2006/061716, dated Oct. 4, 2007. 7 pages.

International Search Report and Written Opinion for PCT Application No. PCT/US2006/061712, dated Oct. 29, 2007. 7 pages.

International Search Report and Written Opinion for PCT Application No. PCT/US2006/061710, dated Feb. 15, 2008. 10 pages.

International Search Report and Written Opinion for PCT Application No. PCT/US2006/061711, dated Oct. 5, 2007. 8 pages.

International Search Report and Written Opinion for PCT Application No. PCT/US2006/061713, dated Oct. 3, 2007. 1 page.

International Search Report and Written Opinion for PCT Application No. PCT/US2006/061717, dated Oct. 4, 2007, 9 pages.

Supplementary European Search Report for EP Application No. 06839102.8, dated Nov. 16, 2009. 7 pages.

Supplementary European Search Report for EP Application No. 06848530,9, dated Nov. 17, 2009. 7 pages.

(56) References Cited

OTHER PUBLICATIONS

Supplementary European Search Report for EP Application No. 06840133.0, dated Nov. 16, 2009. 8 pages.
International Search Report and Written Opinion for PCT Application No. PCT/US2010/034412, dated Jun. 29, 2010. 1 page.
Supplementary European Search Report for EP Application No. 10775417.8, dated Oct. 25, 2013. 5 pages.
International Search Report and Written Opinion for PCT Application No. PCT/US2008/084200, dated Jan. 22, 2009. 1 page.
International Search Report and Written Opinion for PCT Application No. PCT/US2010/034414, dated Sep. 1, 2010. 13 pages.
Supplementary European Search Report for EP Application No. 06839102.8, dated Nov. 16, 2009. 6 pages.
Supplementary European Search Report for EP Application No. 06848530.9, dated Nov. 17, 2009. 6 pages.

\* cited by examiner

METHOD AND APPARATUS FOR DETERMINING TISSUE MORPHOLOGY BASED ON PHASE ANGLE

CROSS-REFERENCE TO RELATED APPLICATIONS

This is a divisional application of U.S. application Ser. No. 11/966,320, filed 28 Dec. 2007, now pending, which is hereby incorporated by reference as though fully set forth herein.

BACKGROUND OF THE INVENTION a. Field of the Invention

The instant invention relates to a method and apparatus for complex impedance compensation, and, in another aspect, a method and apparatus for using complex impedance measurements including a phase angle to detect tissue morphology.

Many applications have been proposed for the use of a measured impedance of tissue, for example cardiac tissue, and not surprisingly a number of approaches for making such impedance measurements have also been proposed. One procedure where an impedance is measured and used is in cardiac catheter ablation.

b. Background Art

As general background, there are a number of methods used for ablation of desired areas, including, for example, radio frequency (RF) ablation. RF ablation is accomplished by transmission of radio frequency energy to a desired target area through an electrode assembly to ablate tissue at the target site. RF ablation may generate significant heat if not controlled. It is therefore known to provide an RF ablation generator with certain feedback features, such as temperature and impedance. To provide such feedback for the physician/clinician's use during the procedure, conventional RF ablation generators are typically configured to measure and display a magnitude of a complex impedance |Z| intended to represent the impedance of the patient's tissue near and around the ablation electrode. To make the impedance measurement, conventional generators use one tip conductor (i.e., one lead through the catheter to the ablation tip electrode) and one ground conductor (i.e., one lead from a ground patch or the like back to the generator). The frequency of the source used to make the impedance measurement is generally the ablation energy source frequency, which can typically vary from 50 kHz to 500 kHz depending on the ablation generator. Such impedance measurements are commonly used to assess tissue heating and tissue-electrode contact levels. However, one shortcoming in the art is that such measurements are subject to variation due to factors unrelated to the condition of the tissue (i.e., non-physiologic changes). For example, coiling of an ablation generator cable during the procedure can increase its inductance and thus alter the impedance measurement, resulting in an inaccurate reading that is not completely indicative of the actual tissue condition. This scenario is particularly problematic where a phase angle of the complex impedance of cardiac tissue is sought, since this parameter is fairly low to begin with (<15°) for the frequencies typically used for RF ablation.

Another shortcoming is that conventional approaches for complex impedance measurements do not provide any intelligence as to tissue morphology, but rather appear to relate to tissue heating and electrode-to-tissue contact levels. An improvement to conventional approaches has been proposed which uses a phase measurement to assess the contact level for the catheter electrode. Tissue is more capacitive and resistive than myocardium due to the cell structure. Therefore, compared with blood, the measured impedance becomes more capacitive and the phase angle becomes more negative when the electrode is in contact with myocardium.

There is therefore a need to minimize or eliminate one or more of the problems set forth above.

BRIEF SUMMARY OF THE INVENTION

It is desirable to be able to provide a method and apparatus for measuring a complex impedance of tissue that can incorporate compensation for changes in the equipment, namely the connecting cable, such as by cable coiling or the like. It is also desirable to provide a method and apparatus to detect tissue morphology using a complex impedance measurement, for example based on a phase angle of the tissue's complex impedance. Detecting a tissue type can be useful in various applications, including diagnosis/therapy of ventricular tachycardia (VT). For example, one of the approaches for VT ablation is to ablate on the border between the scar and normal tissue to isolate VT.

In a first aspect of the present invention, a compensation apparatus is provided directed to overcoming one or more of the problems noted above. In concept, the compensation apparatus is configured to determine a complex impedance attributable to a connecting cable. It then uses this determination to provide compensation for another complex impedance measurement within the same cable. The compensation apparatus is preferably provided for use with a catheter having an electrode and a cable. The cable is configured to allow a first electrical connection to be made between the catheter and an electrical device (e.g., an ablation generator) so as to allow the device to electrically interact with the electrode (e.g., for an ablation procedure). The first electrical connection (the "working connection") is the one that will have the compensation (i.e., the effects of the cable removed).

The compensation apparatus includes a circuit and a compensation control. The circuit has a predetermined complex impedance when probed or excited by a pilot signal having a predetermined frequency. The known-impedance circuit is located in either the handle of the catheter or a distal end of the cable. The compensation control is configured to generate the pilot signal. The cable is arranged to allow a second electrical connection (the "control" connection) to be made between the compensation control and the circuit. The second electrical connection in the cable is the one that will be used to measure the level of undesired (non-physiologic) variations. The compensation control is configured to measure the complex impedance of the combination of the cable (i.e., over the second electrical connection) and the circuit, which has the known impedance. The compensation control is further configured to then determine a difference between the measured and known complex impedances. The difference, if any, thus represents variation due to the cable configuration, may be used for compensating on any complex impedance measurements over the first electrical connection within the same cable.

In a second aspect of the invention, a method for determining a tissue type is provided. In a preferred embodiment, the tissue under test may be one of a plurality of different tissue types, including regular myocardium, scar/ischemia and fat. The method includes the steps of providing a first electrode in contact with the tissue. Next, measuring a complex impedance, at a predetermined frequency, between the first electrode and second electrode such as a reference electrode (patch). The predetermined frequency may be between about 20 kHz and 100 kHz, which reveals the capacitive properties of the tissue, while minimizing contributions by other factors not of interest (e.g., the reactance of any blood, the reactance due to the electrode-electrolyte interface, etc.). The complex impedance includes a magnitude and a phase angle component. Finally, the method includes the step of identifying one of the tissue types based on at least one of the measured magnitude and phase angle components, preferably at least the phase angle component.

The foregoing and other aspects, features, details, utilities, and advantages of the present invention will be apparent from reading the following description and claims, and from reviewing the accompanying drawings.

DETAILED DESCRIPTION OF THE INVENTION

The invention that will be described herein includes two main aspects. In the first aspect, an apparatus and method for complex impedance compensation is provided. The first aspect of the invention overcomes a problem described in the Background, namely, changes in the measured complex impedance that are observed but which are due to changes in the configuration of the equipment, namely the connecting, such as by cable coiling and the like. The first aspect provides the ability to measure the complex impedance with respect to the tissue more accurately, which, as understood by those in the art, will have many useful applications. In the second aspect of the invention, an apparatus and method is provided for determining a tissue type based on, preferably, a phase angle component and/or also a magnitude component of the tissue's complex impedance. The second aspect of the invention is useful in identifying tissue during certain applications, for example, identifying scar tissue in ventricular tachycardia (VT) applications or epicardial applications for locating fat and scar tissue. For VT ablation, one of the current approaches is to ablate on the border between the scar and normal tissue to isolate the scar that triggers VT. As to epicardial RF application, one of the important issues is to apply energy to regular tissue and avoid RF application on fat which does not create an efficacious lesion.

It should be understood that the two aspects of the invention are not limited to the particular illustrated embodiments. For example, the apparatus and method for each may be used with catheters/catheter systems for diagnostic, therapeutic, mapping and/or ablative procedures, to name just a few.

As further background, a complex impedance (Z) can be expressed as set forth in equation (1)

$$Z = R + jX \tag{1}$$

Where R is a resistance component; and X is a reactance component that is based on both capacitance and inductance contributions. A complex impedance can also be expressed as set forth in equation (2):

$$Z = |Z| < \phi \tag{2}$$

Where $|Z|$ is the magnitude of the complex impedance and $\phi$ is called the phase angle or alternatively sometimes simply the "phase." These quantities are defined in equations (3) and (4):

$$|Z| = \sqrt{R^2 + X^2} \tag{3}$$

$$\tan \phi = X/R \tag{4}$$

As used herein, the term complex impedance is taken to include a magnitude and a phase angle. Where a magnitude of the complex impedance is intended, an absolute value of Z will be denoted, $|Z|$. With this background, the first and second aspects of the invention will now be set forth.

Impedance Compensation for Catheters and Cables

Figure 1:
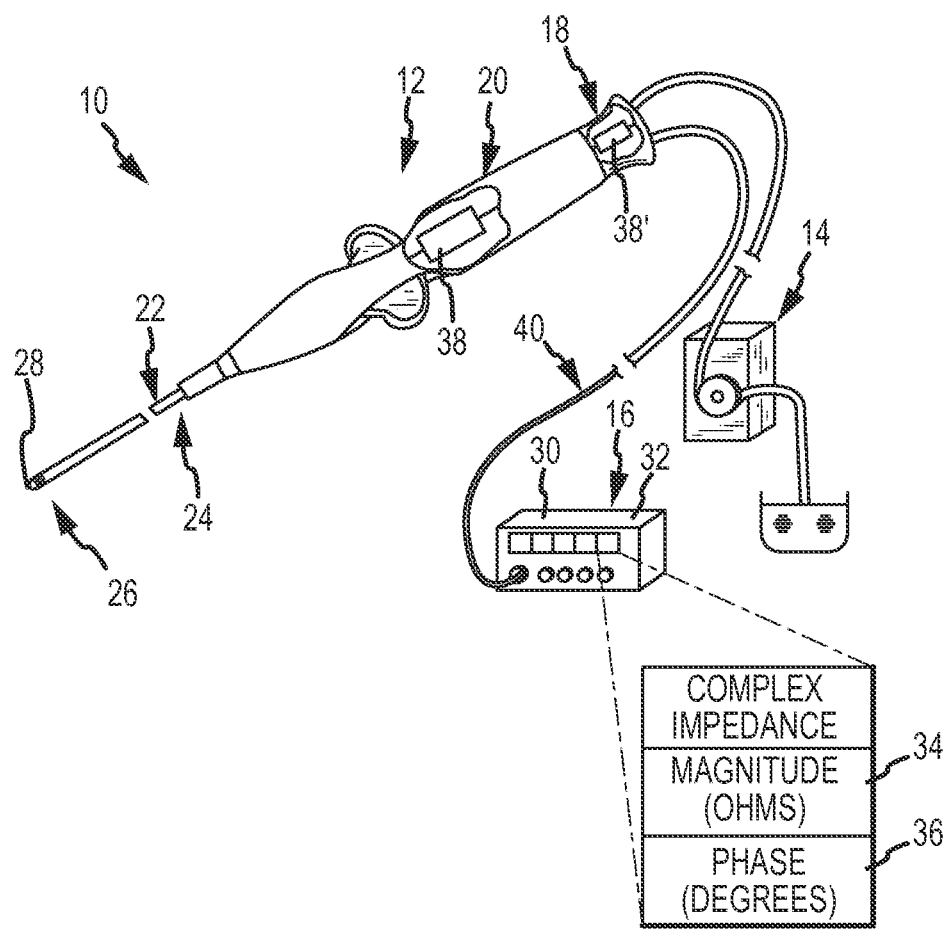
FIG. 1 is a diagrammatic view of an RF ablation embodiment having complex impedance compensation in accordance with the present invention.

Referring now to the drawings wherein like reference numerals are used to identify identical components in the various views, FIG. 1 is a simplified, perspective view of an exemplary system 10 for conducting a diagnostic or therapeutic function, in which the first aspect (impedance compensation) may be practiced. In particular, the first aspect provides the capability to compensate for complex impedance variations due to the cable. The first aspect, generally, involves deploying a circuit, one with a known complex impedance, and then measuring the complex impedance of that circuit over a first electrical connection through a cable. Any measured variations from the known, complex impedance can then be attributed to the cable. Recall, the connecting cable may be a source of variation in measured complex impedance due to non-physiologic changes (e.g., cable coiling, cable being wrapped around a steel bedpost to form an inductor, etc.). The variation attributed to the cable can then be cancelled out of other measurements in the same cable, for example, when making a complex impedance measurement of tissue over another electrical connection in that same cable. In the exemplary RF ablation embodiment, a first electrical connection, to which the compensation will be applied, is an RF ablation source connection from an RF ablation generator through a generator cable to the ablation catheter. It is typical to make an impedance measurement through this connection. A second electrical connection through the same cable is set up for the purposes of determining what, if any, changes in complex impedance may be due to the cable. It should be understood, however, that this configuration is exemplary in nature only, and that many other arrangements may be practiced, consistent with the teachings of the present invention.

With continued reference to FIG. 1, in the exemplary RF ablation embodiment, a system 10 is shown to include a catheter 12 operably connected to a fluid source 14, such as a pump assembly, and an energy source, such as an RF ablation generator 16. The fluid source 14 and the RF ablation generator 16 may serve to facilitate the operation of ablation procedures and may involve monitoring any number of chosen variables (e.g., temperature of ablation electrode, ablation energy, and position of the assembly), assisting in manipulation of the assembly during the use, and providing the requisite energy source. Furthermore, additional components may be integrated into the system 10, such as visualization, mapping and navigation components known in the art, including among other things, NavX® or other systems. Moreover, it should be understood that embodiments consistent with the present invention may, and typically will, include other features not shown or described herein for the sake of brevity and clarity. For example, an ablation catheter may typically include additional electrodes (and corresponding leads), a temperature sensor (and corresponding leads), and other features as known in the art.

The catheter 12 may include a cable connector or interface 18, a handle 20 and a shaft 22 having a proximal end 24 and a distal end 26 near which an ablation electrode 28 is disposed. It should be re-iterated that while one electrode 28 is shown, the catheter 12 may include a plurality of electrodes, and that in any event, the electrode 28, in other embodiments (other than RF ablation) may be used for any number of diagnostic and/or therapeutic purposes. For instance, such electrodes and therefore such catheters may be used for performing ablation procedures, cardiac mapping, electrophysiological (EP) studies, and other like procedures. Accordingly, the present invention is not limited to any one type of catheter or catheter-based system or procedure.

The general structural and functional features of catheter systems such as those generally comprising the catheter 12, the fluid source 14 and the RF ablation generator 16 are generally well known to those of skill in the art. For example, the fluid source 14 can comprise various known assembly, including fixed volume rolling pumps, variable volume syringe pumps and other pump assembly known to those skill in the art. Moreover, the fluid provided by fluid source 14 may comprise a suitable biocompatible fluid, such as saline. Subject to the modifications described below, the RF ablation generator 16 may comprise conventional apparatus, such as a commercially available unit sold under the model number IBI-1500T RF Cardiac Ablation Generator, available from Irvine Biomedical, Inc. Of course, the RF ablation generator 16 can also comprise various other known energy sources.

With continued reference to FIG. 1, the RF ablation generator 16 includes an RF power source 30 configured to generate an ablation signal. The RF ablation signal may typically have a frequency within the range of 50 kHz and 500 kHz. The ablation generator 16 further includes an impedance determining circuit 32 configured to determine a complex impedance of a tissue volume proximate the tip electrode 28. As shown, the complex impedance may comprise a magnitude component 34 (e.g., expressed in ohms) and a phase angle component 36 (e.g., expressed in degrees). The power source 30, as described above, may comprise conventional components. The impedance determining circuit 32 may also comprise conventional components known in the art, subject to the modifications described herein.

FIG. 1 further shows a circuit 38, which in one embodiment is located in the handle of the ablation catheter 12, and in another embodiment (circuit 38') is alternatively located in the distal end of a generator cable 40. As used herein, unless otherwise stated, both circuits 38 and 38' are the same (only the location is different). Therefore, where further reference is made to circuit 38 it should be understood that such reference also applies to circuit 38'. In either case, the circuit 38 (or 38') has a predetermined, known complex impedance when probed or excited by a pilot signal having a predetermined frequency. The predetermined frequency may preferably be between 100 Hz and 1 MHz, more preferably between 6 kHz and 50 kHz, and still more preferably be about 20 kHz. In various embodiments, the circuit 38 may be one selected from the group including: a loop-back circuit (i.e., a short circuit), a series-connected resistor circuit, series-connected resistor-inductor (RL) circuit, a series-connected resistor-capacitor (RC) circuit, a series-connected resistor-inductor-capacitor (RLC) circuit, a parallel-connected RL circuit, a parallel-connected RC circuit, a parallel-connected RLC circuit or a combination of any of the foregoing. It should be appreciated that when the R, L and C values are all set to zero, the circuit 38 simplifies to the loop-back circuit described above, which still satisfies the property of having a known, complex impedance (i.e., one would expect relatively low resistance with negligible phase shift for a loop-back).

Figure 2:
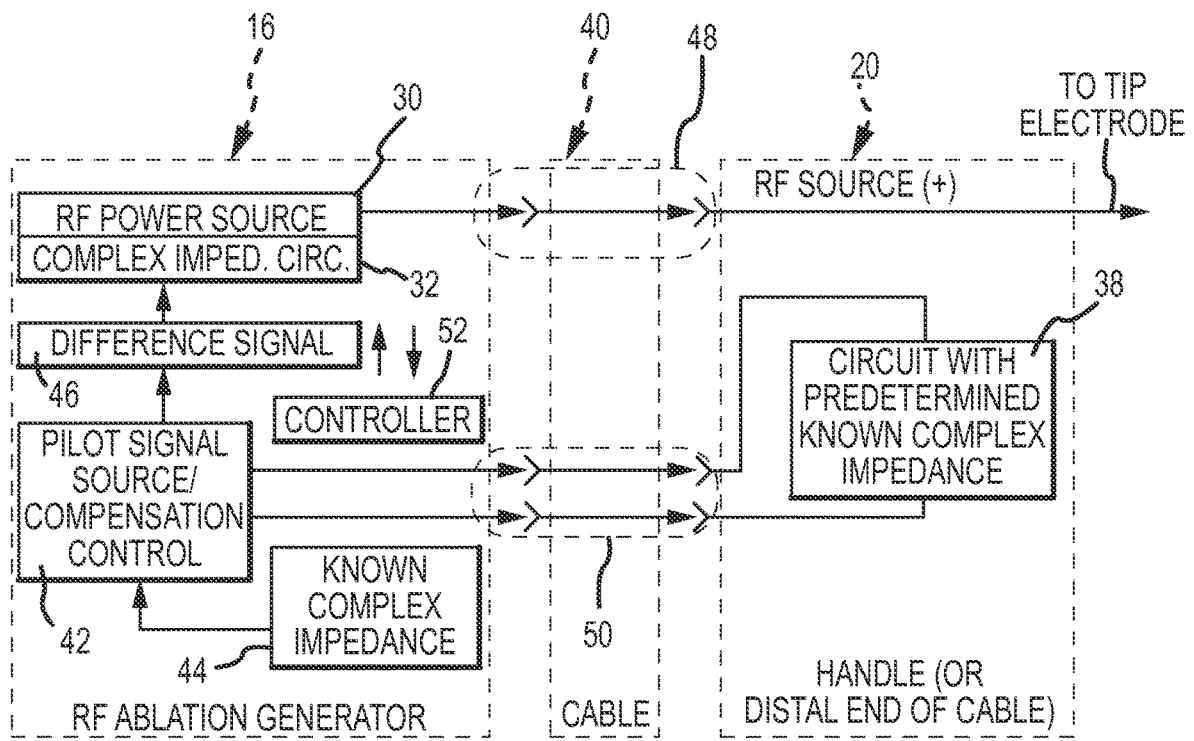
FIG. 2 is a simplified block diagram showing, in greater detail, the complex impedance compensation apparatus of FIG. 1.

FIG. 2 is a simplified block diagram showing, in greater detail, an arrangement for complex impedance compensation. In one embodiment, a compensation control 42 is provided, which may be integrated within the ablation generator 16; however, in an alternate embodiment, the compensation control 42 may be provided as a separate unit. FIG. 2 further shows a known complex impedance block 44 (i.e., a block that provides the magnitude/phase values known for the circuit 38), a difference signal 46, a first electrical connection 48 over the cable 40 and a second electrical connection 50 that is independent from the first electrical connection 48 but is also over the same cable 40.

As shown, the cable 40 is configured generally to allow the first electrical connection 48 to be made between the RF ablation source 30 and the catheter 12 (i.e., and in turn to the ablation tip electrode 28). The first electrical connection 48 is the connection for which compensation will be made. Additionally, the cable 40 is configured to allow the second electrical connection 50 to be made between the compensation control 42 and the known-impedance circuit 38. The second electrical connection 50 is the connection upon which the difference signal 46 (i.e., a compensation or cancellation factor) will be determined. While the second connection 50 is illustrated in exemplary fashion as having two wires, it should be understood that the invention is not so limited. More than two wires may be used to form the second electrical connection 50, and likewise, a single wire may be employed.

The compensation control 42 is configured to generate the above-described pilot signal at the predetermined frequency for probing or exciting the circuit 38. Specifically, the compensation control 42 is configured to measure the complex impedance of the combination of the second electrical connection 50 and the circuit 38. Since the complex impedance of the circuit 38 is known and available in advance, the compensation control 42 is further configured to determine a difference between the measured complex impedance and the predetermined (known) complex impedance of the circuit 38. Any difference, be it expressed in terms of a magnitude (e.g., ohms), a phase angle (e.g., degrees) or both, would then be deemed attributable to the configuration of the cable 40. The compensation control 42 is thus further configured to generate the difference signal 46 indicative of the difference as determined by the control 42. For example, if the measured complex impedance, when taken relative to the predetermined, known complex impedance, indicates an additional phase lag of X degrees due to cable coiling or the like adding inductance, the difference signal 46 may be generated to indicate the additional X degrees lag. The difference signal 46 is provided to the complex impedance determining circuit 32, which is configured to use the difference signal 46 in making compensatory adjustments. Specifically, the circuit 32 is configured to use the difference signal 46 to cancel or null out cable configuration-related variations in any measured complex impedance taken over the first electrical connection 48. The particulars of the difference signal may take many forms, although it should be understood that the selected form will be coordinated with the form expected by the complex impedance determining circuit 32.

The compensation control 42, in one embodiment, may be a computer-implemented apparatus operating under software control. For this purpose, a controller 52 (which may already be present in the ablation generator 16 if integrated) may be configured to execute pre-programmed instructions to perform the various functions described herein. The compensation control 42 may include various controlled hardware, such as a pilot source generator to generate the pilot signal, as well as structure suitable for measuring the resultant signal induced by the application of the pilot signal over the second electrical connection 50 to the circuit 38. These structures may comprise conventional apparatus well known to those of ordinary skill in the art. In the computer-implemented embodiment, the difference signal 46 may take the form of a compensation factor or parameter, which may be stored in a memory and available for access by the impedance determining circuit 32. Additionally, the compensation control 42 may be further configured to update the difference signal 46 on a periodic basis, so as to provide real-time complex impedance compensation.

In an alternate embodiment, the compensation control 42 may be implemented completely in hardware employing various means to measure a difference in magnitude and phase (e.g., phase detector) between the measured complex impedance (i.e., the cable plus the circuit 38) and the predetermined known complex impedance of the circuit 38.

Figure 3:
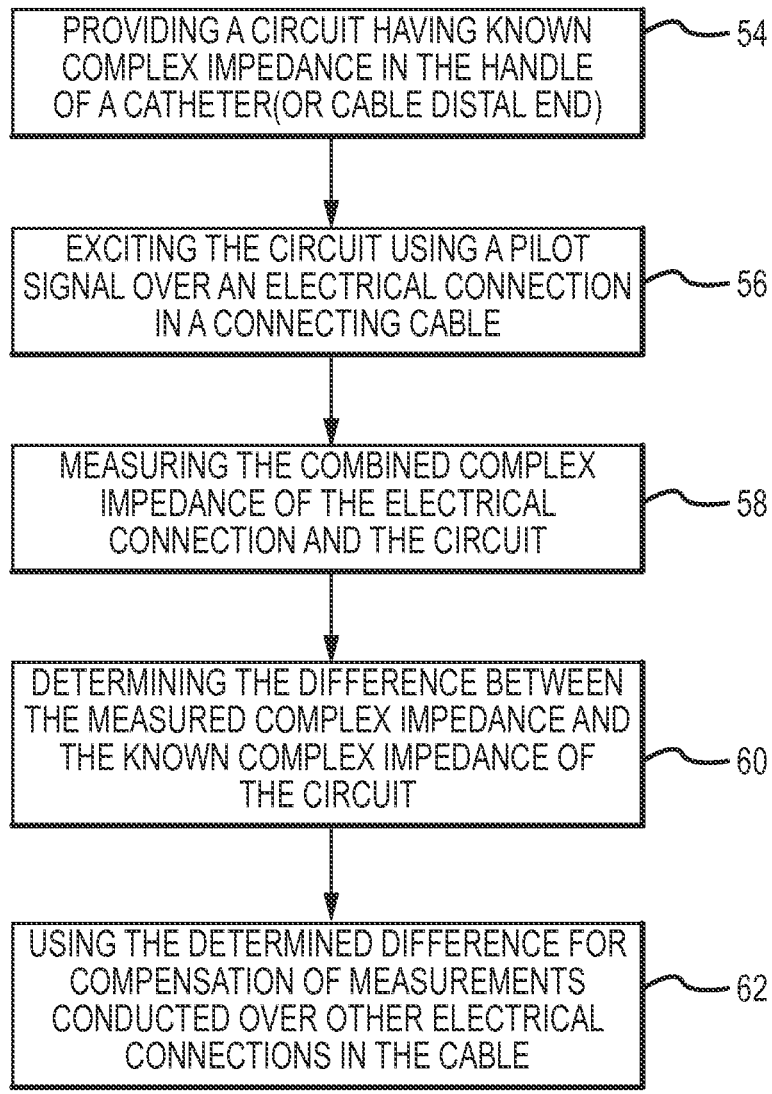
FIG. 3 is a flow chart diagram showing a method for complex impedance compensation in accordance with the present invention.

FIG. 3 is a flowchart showing a method for complex impedance compensation in accordance with the present invention. The method begins in step 54.

Step 54 involves the step of providing a circuit (e.g., the circuit 38) having a known, predetermined complex impedance at a predetermined frequency of interest (see above description of the predetermined frequency). The circuit 38 may be located in the handle of a catheter, or in the distal end of a connecting cable. The criteria for locating the circuit 38 is to include as much of the cable, preferably all of the cable, in the complex impedance measurement. The method proceeds to step 56.

Step 56 involves the step of probing or exciting the circuit 38 using the pilot signal at the predetermined frequency over an electrical connection (e.g., the electrical connection 50) in the cable 40. The method proceeds to step 58.

Step 58 involves the step of measuring the combined complex impedance of the electrical connection 50 and the circuit 38. The method proceeds to step 60.

Step 60 involves the step of determining a difference between the measured complex impedance (cable plus circuit 38) and the predetermined, known complex impedance of the circuit 38. This difference may be a phase angle shift (degrees), a difference in magnitude (ohms), or both. The method then proceeds to step 62.

Step 62 involves the step of using the determined difference for compensation purposes in measurements (e.g., complex impedance measurements) conducted over other electrical connections in the same cable. For example, the complex impedance may be measured through the first electrical connection using the catheter electrode. Then, the difference may be cancelled out of such other complex impedance measurement, thereby removing the effect of the cable configuration. Through the foregoing, changes that might occur in the cable can be quantified and removed, leaving only the accurate measurement intended (e.g., the complex impedance measurement of the subject tissue).

While the first aspect for an inventive compensation scheme was described in connection with an RF ablation system, it should be understood that this aspect of the invention is not so limited, and may be employed in a variety of other configurations where a catheter and one of its electrodes is used to conduct a diagnostic or therapeutic function.

Determining Tissue Morphology Based on Phase Angle

In the second aspect of the invention, an apparatus and method is described for determining tissue morphology based on a phase angle and/or additionally a magnitude of the tissue's complex impedance. In the field of cardiac catheter ablation, "impedance" conventionally means the magnitude Z of the complex impedance.

In the context of RF ablation, which is typically conducted at around 500 kHz, a working assumption is that such procedures involve nearly purely resistive heating. However, there does exist a number of sources that contribute capacitance. At least three main sources of such capacitance include: (1) blood; (2) the subject tissue; and (3) an electrode (e.g., Pt/Ir)-electrolyte (blood or saline) interface. Additional sources of capacitance include any connecting wires as well as stray capacitance. When the ablation system impedance is measured (e.g., by using an LCR impedance meter), a phase angle (or reactance component) is registered in addition to a resistance component (e.g., $Z=R+jX$). The reactance due to the capacitance and inductance is typically much smaller than the resistance, and the phase angle is relatively small as well (e.g., <15°). Accordingly, for most conventional purposes, such as determining tissue heating for example, the assumption that RF ablation conducted at ~500 kHz or similar frequencies is resistive is adequate. However, for other purposes, such as the inventive approach for detecting a tissue type, this assumption is inadequate.

Investigation has shown that the three sources of capacitances described above change differently as a function of frequency. While the reactance contributed by the blood capacitance and the electrode-electrolyte interface capacitance both decrease to zero when excited at frequencies above 20 kHz (becoming essentially resistive), this is not the case with tissue. The capacitance of tissue provides a significant reactance value into the 100 kHz frequency range and does not decrease to near zero until above 500 kHz or higher, which is believed due to cell membranes contributing capacitance.

During cardiac catheter ablation, one of a plurality of different tissue types may be encountered. In the context of the exemplary embodiment, regular myocardium, scar and fat tissue types are typical of the types of tissue that can be encountered, although it should be understood that other tissue types may be appropriate for other embodiments according to the principles disclosed herein.

It is important to understand the underlying structure of the different tissue types and how such different structures affect its respective complex impedance characteristics. First, the cell structure for regular myocardium is different from that of other types of tissue considered herein such as scar and fat tissue. The major determinants affecting complex impedance of regular myocardial tissue are the extra-cellular and intra-cellular resistance, a gap junction conductance, and the cell membrane capacitance (already mentioned above). Regular myocardium therefore presents a moderate impedance (magnitude) and a regular phase angle value (negative). Scar tissue is common for ventricular tachycardia (VT) and is considered inexcitable and acellular. This makes the scar tissue more conductive and less capacitive due to lack of cell membrane, which results in low impedance and low phase angle (negative). Both the low impedance and the low phase angle of scar tissue are different from regular myocardium. Finally, fatty tissue is considered non-conductive because of the fat content, and accordingly has even higher impedance than myocardium. Fat, however, has a lower phase value because no capacitive cell membrane is present. It should be understood that the impedance (magnitude) and phase angle values for these tissue types are relative to each other. Accordingly, no specific values are necessary.

Based on the foregoing, a correlation can be made between the phase angle, on the one hand, and the tissue type, on the other hand. More specifically, based on both impedance |Z| and the phase angle $\phi$, a tissue type can be determined for tissue near a measurement electrode(s), as set forth in Table 1.

TABLE 1

|  | Magnitude (Impedance) |Z| | Phase Angle $\phi$ |
|---|---|---|
| Regular myocardium | Medium | High |
| Scar/ischemia | Low | Low |
| Fat | High | Low |

Thus, using the foregoing measurement technique, a high impedance and low phase angle indicates fatty tissue. Alternatively, low impedance and low phase angle indicates a scar. Moderate impedance value (i.e. between fat and scar) and a high phase angle value indicate normal myocardium. It is important to note that phase angle values in the aforementioned paragraphs are all negative, such that a high phase angle means more negative phase angle.

According to this aspect of the invention, use of the phase angle $\phi$ in distinguishing tissue types is preferred because it exhibits a different and unique response for each tissue type: regular myocardium, scar and fat. Additionally, the complex magnitude ("impedance") |Z| may be further used as well to distinguish regular tissue from irregular tissue, or even scar from fat, based on the particular values of the impedance measurements. Normally, fat is more resistive than scar tissue and this property can be used to differentiate scar from fat.

Figure 4:
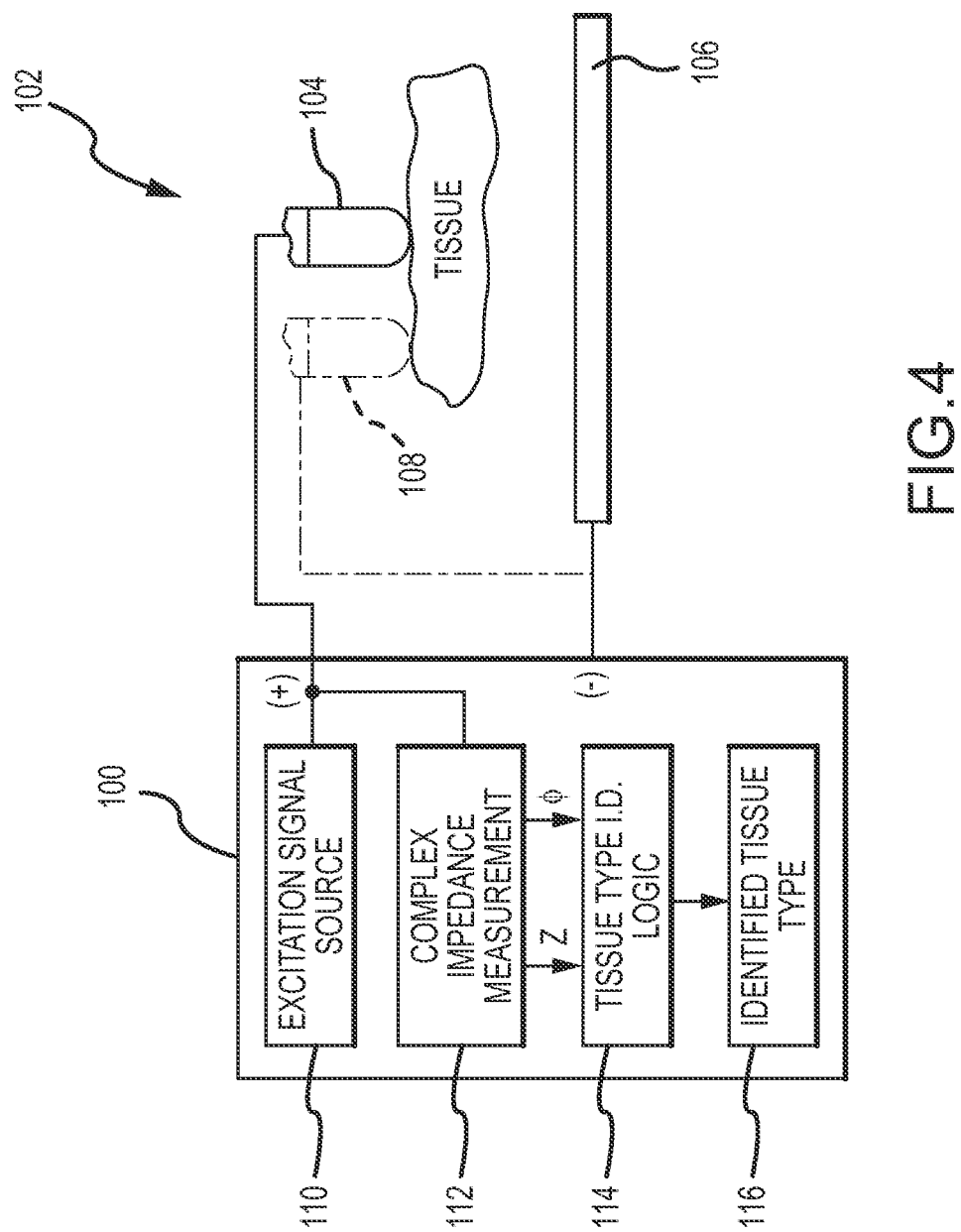
FIG. 4 is a simplified diagrammatic and block diagram of an apparatus for determining a tissue type in accordance with the present invention.

FIG. 4 is a simplified block diagram of an apparatus 100 configured to determine a tissue type based on a phase angle and/or magnitude of a measured complex impedance of the tissue. The apparatus 100 is configured for use with a catheter system 102 (partially illustrated) that includes a first electrode 104. The catheter system 102 is configured to position the first electrode 104 so as to be in contact with the body tissue whose type is to be identified. The magnitude and phase angle measurements are dependent on the electrode contact level. Therefore, to enhance the electrode contact level and thus assure accurate complex impedance measurements, the first electrode 104 is preferably, although not exclusively, contemplated to be relatively small in size, such as the following (or smaller): between a Five French (5 Fr) and Ten French (10 Fr) in diameter, more preferably a Five French (5 Fr) in diameter, and between 2 and 8 mm in length. FIG. 4 further shows a second electrode, which in a first embodiment is a reference electrode 106, such as a ground patch or the like, that is relatively large in size compared to the first electrode 104. Patch 106 may be of the dispersive/indifferent electrode pad type. In this first embodiment (small first electrode plus patch), the complex impedance measurement being made reflects the properties of the tissue near and around the first electrode 104. In an alternate embodiment, the second electrode may be another relatively small electrode, such as a tip electrode 108 or the like, shown in phantom line in FIG. 4. The second electrode 108 may be of the same configuration as the first electrode 104. In this alternate embodiment (i.e., two small electrodes), the complex impedance measurement being made reflects the properties of the tissue between the first and second electrodes 104, 108. In still further embodiments, additional, relatively small electrodes similar to electrode 104 may be further included.

The apparatus 100 includes an excitation signal source 110, a complex impedance measurement block 112, and a tissue type identification logic block 114 configured to determine and output a tissue type 116. The excitation signal source 110 is coupled, effectively, across the first and second electrodes 104 and 106 (or alternatively 108) and is configured to generate the excitation signal used in determining the complex impedance. More particularly, the excitation signal, when applied across the electrodes, will produce a corresponding induced signal whose characteristics will be determined by, and thus be indicative of, the properties of the tissue under test. In one embodiment, the excitation signal has a predetermined frequency preferably between about 20 kHz or greater and 1000 kHz or less, and more preferably between about 50 kHz or greater and 500 kHz or less. The excitation signal source 110 may comprise conventional apparatus for generating such a signal (e.g., may be either a constant voltage or current at the predetermined frequency).

The complex impedance measurement block 112 is coupled, effectively, across the first and second electrodes 104 and 106 (or alternatively 108) and is configured to determine a complex impedance therebetween, based on the measurement of the induced signal, in view of the applied excitation signal. The block 112 may comprise conventional apparatus for performing such measurements, in view of the selected nature and format of the applied excitation signal. The source 110 and the measurement block 112 may be integrated (e.g., like an LCR meter).

The block 114 is configured to identify one of a plurality of candidate tissue types based on at least one of the phase angle and/or magnitude of the tissue's complex impedance. The block 114 is further configured to produce an output 116 reporting the identified tissue type. The block 114 may be implemented with conventional apparatus known to those of ordinary skill in the art, and may be a computer-implemented apparatus (a computer-based controller not shown) configured to operate in accord with pre-programmed instructions and data. The block 114 may thus be preconfigured to include a data structure (data structure not shown) and/or logic reflecting the relationship(s) between tissue type, on the one hand, and the expected phase angles and/or magnitudes on the other hand, such as illustrated in Table 1 for regular myocardium, scar and fat. In a preferred embodiment, the plurality of candidate tissue types includes regular myocardium, scar and fat as particularly set forth in Table 1. Practicing this aspect of the invention in software would require no more than ordinary skill in the art, in view of this enabling disclosure describing the functions to be performed. Of course, other implementations are possible, consistent with the teachings disclosed herein.

Figure 5:
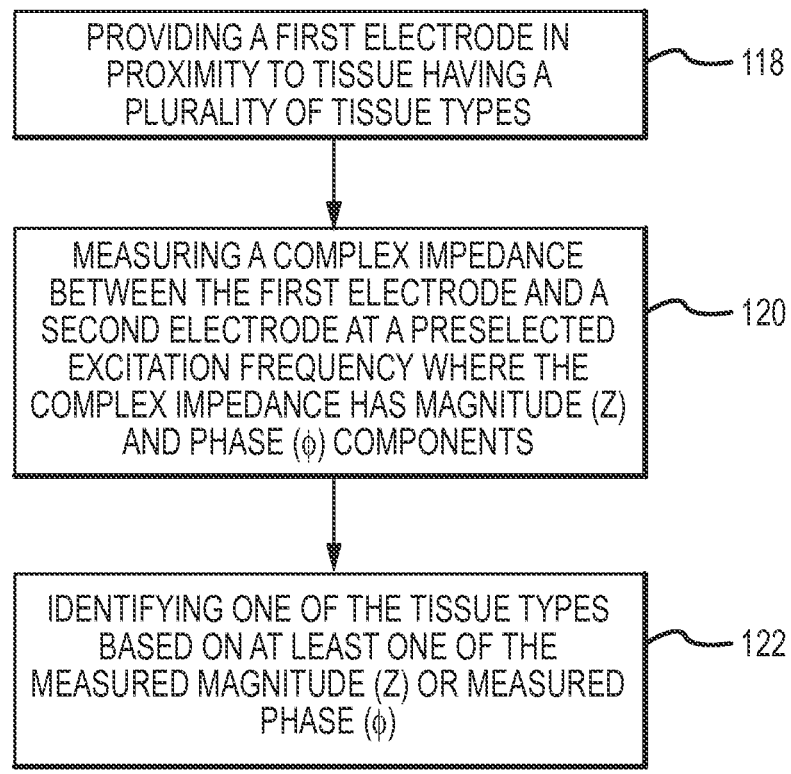
FIG. 5 is a flow chart diagram showing a method for determining a tissue type in accordance with the present invention.

FIG. 5 is a flowchart diagram of a method of determining a tissue type. The method begins in step 118.

Step 118 involves the step of providing a first electrode (e.g., first electrode 104) in adequate contact with tissue where the tissue may be one of a plurality of expected, candidate tissue types. Step 118 also involves providing a second electrode, such a reference electrode patch 106 or alternatively the second electrode 108 (as described above). The method then proceeds to step 120.

Step 120 involves the step of measuring a complex impedance between the first and second electrodes using an excitation signal having a predetermined frequency. Step 120 may include the substep of selecting a value defining what specific frequency to use, the particulars of which have been described above. Additionally, the complex impedance comprises a magnitude ("impedance") |Z| and a phase angle φ. The method proceeds to step 122.

Step 122 involves the step of identifying one of the plurality of candidate tissue types based on at least one of the magnitude and/or phase angle. In the embodiment described herein involving the candidate tissue types of regular myocardium, scar and fat, the phase angle φ is the preferred, primary parameter. The magnitude |Z| may be employed as a secondary parameter, all as described above in detail. Step 122 may further include the substep of reporting the identified tissue type. Through the foregoing, an apparatus and method is provided for determining a tissue type, based on the phase angle and/or magnitude of the tissue's complex impedance. The apparatus and method is useful in many applications, including VT applications described above.

Although numerous embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of determining tissue type and ablating comprising the steps of:

defining a plurality of tissue types to include regular myocardium, scar and fat;

correlating each one of the tissue types with both a respective phase angle value and magnitude value associated with a complex impedance of each of said tissue types to thereby define a first relationship between said regular myocardium tissue type and a high phase angle value and a medium magnitude, a second relationship between said scar tissue type and a low phase angle value and a low magnitude value, and a third relationship between said fat tissue type and a low phase angle value and a high magnitude value, and wherein said high phase angle value is higher than said low phase angle value, and wherein said medium magnitude value is between said high and low magnitude values;

providing a first electrode in contact with tissue where the tissue may be one of said plurality of tissue types including regular myocardium, scar and fat;

providing a second electrode, measuring a complex impedance at a preselected excitation frequency between the first electrode and the second electrode where the measured complex impedance comprises a magnitude and a phase angle;

selecting one of the first, second, and third relationships based directly on both the measured phase angle value from the measured complex impedance and the measured magnitude value from the measured complex impedance;

identifying, using a tissue type identification logic block implemented on a computer-based controller, one of regular myocardium, scar and fat tissue types based on the selected one of said first, second, and third relationships wherein the tissue type identification logic block produces an output indicative of the identified tissue type; and applying, using an ablation generator responsive to the output indicative of the identified tissue type, ablation energy to the tissue when the identified tissue type is regular myocardium.

2. The method of claim 1 wherein said step of providing the first electrode includes the substeps of:

selecting a size between Five French (5 Fr) and Ten French (10 Fr) in diameter and 2 to 8 mm in length for the first electrode.

3. The method of claim 1 wherein said step of providing the first electrode includes the substeps of:

introducing the first electrode using a catheter during a cardiac catheter ablation procedure for contact with the tissue.

4. The method of claim 1 wherein said step of measuring the complex impedance includes the substep of:

selecting, the excitation frequency from a range between 20 kHz and 1000 kHz.

5. The method of claim 4 wherein said range is between 50 kHz and 500 kHz.

6. The method of claim 1 wherein said second electrode is a dispersive/indifferent reference electrode, said measured complex impedance reflecting properties of tissue proximate said first electrode.

7. The method of claim 1 wherein said first and second electrodes are each electrodes in contact with the tissue, said measured complex impedance reflecting properties of tissue between the first and second electrodes.

8. An apparatus for determining one of a plurality of tissue types and for ablating, said apparatus comprising;

a source configured to supply an excitation signal at a predetermined frequency to a catheter for application at a first electrode of the catheter;

a measurement circuit configured to measure a complex impedance between said first electrode and a second electrode responsive to said excitation signal being supplied where said measured complex impedance comprises a magnitude and a phase angle; and a tissue identification logic block configured to identify one of said plurality of tissue types including regular myocardium, scar and fat, said logic block comprising a correlation for each one of the tissue types with both a respective phase angle value and magnitude value associated with a complex impedance of each of said tissue types to thereby define a first relationship between said regular myocardium tissue type and a high phase angle value and a medium magnitude, a second relationship between said scar tissue type and a low phase angle value and a low magnitude value, and a third relationship between said fat tissue type and a low phase angle value and a high magnitude value, and wherein said high phase angle value is higher than said low phase angle value, and wherein said medium magnitude value is between said high and low magnitude values, said logic block being further configured to select one of said first, second, and third relationships based directly on both the measured phase angle value and the measured magnitude value, said logic block being further configured to identify one of regular myocardium, scar and fat tissue types based on said selected one of said first, second, and third relationships; and an RF ablation generator configured to generate an ablation signal so as to allow ablation of tissue when the tissue identification block identifies the tissue type of the tissue as being regular myocardium.

9. The apparatus of claim 8 wherein a size of said first electrode is between Five French (5 Fr) and Ten French (10 Fr) in diameter and 2 to 8 mm in length.

10. The apparatus of claim 8 wherein said preselected frequency of said excitation signal is between 20 kHz and 1000 kHz.

11. The apparatus of claim 10 wherein said preselected frequency is between 50 kHz and 500 kHz.

12. The apparatus of claim 8 wherein said second electrode is a dispersive/indifferent reference electrode, said measured complex impedance reflecting properties of tissue proximate said first electrode.

13. The apparatus of claim 8 wherein said first and second electrodes are in contact with said tissue, said measured complex impedance reflecting properties of tissue between said first and second electrodes.

14. A method for determining a type of a tissue that may be one of a plurality of types and for ablating, comprising the steps of:
(A) defining a plurality of tissue types to include regular myocardium, scar and fat;
(B) correlating each one of the tissue types with both a respective phase angle value and magnitude value associated with a complex impedance of each of said tissue types to thereby define a first relationship between said regular myocardium tissue type and a high phase angle value and a medium magnitude, a second relationship between said scar tissue type and a low phase angle value and a low magnitude value, and a third relationship between said fat tissue type and a low phase angle value and a high magnitude value, and wherein said high phase angle value is higher than said low phase angle value, and wherein said medium magnitude value is between said high and low magnitude values;
(C) measuring a phase angle component and a magnitude component of a complex impedance of the tissue by applying an excitation signal having a frequency between 20 kHz and 100 kHz to an electrode that is in contact with the tissue and measuring the response signal induced thereby to determine the measured phase angle value and magnitude value;
(D) selecting one of the first, second, and third relationships based directly on both the measured phase angle value and the measured magnitude value;
(E) identifying, using a tissue type identification logic block implemented on a computer-based controller, one of the regular myocardium tissue type, scar tissue type, and fat tissue type based on the selected one of said first, second, and third relationships wherein the tissue type identification logic block produces an output indicative of the identified tissue type; and
(F) applying, using an ablation generator responsive to the output indicative of the identified tissue type, ablation energy to the tissue when the identified tissue type is regular myocardium.

* * * * *